United States Patent
Emonds-Alt et al.

(10) Patent No.: US 6,420,388 B1
(45) Date of Patent: Jul. 16, 2002

(54) OSANETANT IN THE TREATMENT OF DEPRESSION AND DEPRESSIVE DISORDERS

(75) Inventors: Xavier Emonds-Alt, Combaillaux; Philippe Soubrie, Valflaunes; Régis Steinberg, Prades le Lez, all of (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/958,266

(22) PCT Filed: Apr. 11, 2000

(86) PCT No.: PCT/FR00/00924

§ 371 (c)(1), (2), (4) Date: Oct. 5, 2001

(87) PCT Pub. No.: WO00/61125

PCT Pub. Date: Oct. 19, 2000

(30) Foreign Application Priority Data

Apr. 13, 1999 (FR) .............................. 99 04699

(51) Int. Cl.⁷ ............................................. A61K 31/445
(52) U.S. Cl. ....................................................... 514/316
(58) Field of Search ........................................ 514/316

(56) References Cited

U.S. PATENT DOCUMENTS

| | | |
|---|---|---|
| 5,641,777 A | 6/1997 | Emonds-Alt et al. |
| 5,741,910 A | 4/1998 | Bichon et al. |
| 5,942,523 A | 8/1999 | Bichon et al. |
| 6,028,082 A | 2/2000 | Bichon et al. |
| 6,124,316 A | 9/2000 | Bichon et al. |

FOREIGN PATENT DOCUMENTS

| | | |
|---|---|---|
| EP | 673928 | 9/1995 |
| WO | WO 97/10211 | 3/1997 |
| WO | WO 98/11090 | 3/1997 |

OTHER PUBLICATIONS

Ribeiro et al., Neuropeptides, vol. 33, No. 2, pp. 181–188 (1999).

DrugNL Abstract No. 97:4331 (1997).

Khawaja et al., Int. J. Biochem. Cell. Biol., vol. 28, No. 7, pp. 721–738 (1996).

Baby et al., J. Clinical Pharmacy and Therapeutics, vol. 24, No. 6, pp. 461–469 (1999).

PharmPat Abstract No. 18004 (1998).

Drugupdates Abstract No. 94:2579 (2000).

Primary Examiner—William R. A. Jarvis
(74) Attorney, Agent, or Firm—Michael D. Alexander; Paul E. Dupont

(57) ABSTRACT

The invention relates to a method for the treatment of mood disorders utilizing osanetant or a pharmaceutically acceptable salt thereof.

7 Claims, No Drawings

OSANETANT IN THE TREATMENT OF DEPRESSION AND DEPRESSIVE DISORDERS

This application is a 371 of PCT/FR00/00924, filed Apr. 11, 2000.

The subject of the present invention is a novel use of osanetant.

Osanetant is the International Non-proprietary Name (INN) of (R)-(+)-N-[(3-(1-benzoyl-3-(3,4-dichlorophenyl) piperidin-3-yl)propyl)-4-phenylpiperidin-4-yl]-N-methyl acetamide, which has the following formula:

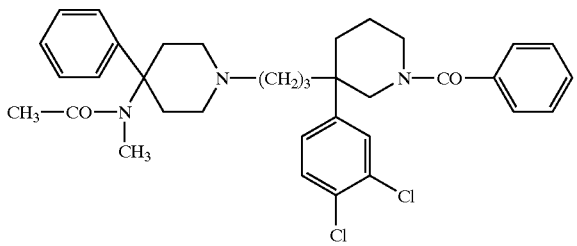

(I)

This compound and its pharmaceutically acceptable salts are described in European Patent Application EP 673 928.

These compounds are described as being selective antagonists of the human $NK_3$ receptor which are useful for the treatment of disorders associated with dysfunction of the dopaminergic and noradrenergic systems.

It has now been found that osanetant and its pharmaceutically acceptable salts are useful for the treatment of mood disorders, in particular for the treatment of depression. By depression is meant in particular, major depressive disorders, minor depressive disorders, dysthymia, depressive disorders associated with anxiety and depressive disorders associated with bipolar disorders.

The effect of osanetant on major depressive disorders has been investigated in patients of between 18 and 65 years of age. The patients were given osanetant (200 mg/day) for a period of about 6 weeks.

The improvement in the depressive syndrome was measured from the significant reduction in the scores on the Hamilton scale (J. Neurol. Neurosurg. Psychiatr., 1960, 23, 56–62) and by recording the impressions of the clinician and the patient's overall impressions.

Thus, the object of the present invention is the use of osanetant and its pharmaceutically acceptable salts for the preparation of medicinal products for use in the treatment of mood disorders, in particular in the treatment of depression.

Osanetant and its pharmaceutically acceptable salts are prepared according to European Patent Application EP 673 928; similarly, the pharmaceutical preparations can be prepared as described in this same patent application.

In the pharmaceutical compositions of the present invention for oral, sublingual, subcutaneous, intramuscular, intravenous, transdermal, local or rectal administration, the active ingredient, either alone or in combination with another active ingredient, can be administered as a unit form for administration, combined with conventional pharmaceutical excipients, to both animals and human beings. The appropriate unit forms for administration include the form for administration by oral route, such as tablets, capsules, powders, granules and solutions or suspensions for oral administration, forms for sublingual and buccal administration, aerosols, implants, forms for subcutaneous, transdermal, intramuscular, intravenous, intranasal and rectal administration.

The daily dosage of the compound according to the invention is from 0.05 to 5 mg/kg, advantageously from 1 to 2.5 mg/kg, preferentially from 2 to 2.5 mg/kg, to be administered once or several times a day. The compounds are generally formulated as dosage units containing from 2.5 to 500 mg, advantageously from 50 to 250 mg, preferentially from 100 to 250 mg, of the active ingredient per unit dose, to be administered once, twice or several times, as required. Although these dosages are examples of typical situations, in special circumstances higher or lower doses may be appropriate, and these dosages are also included in the invention. According to the usual practice, the appropriate dosage for each patient is determined by the physician according to the method of administration, age, bodyweight and response of the said patient.

According to the present invention, the oral forms for administration are preferred.

The compounds according to the invention can be administered concomitantly with another active ingredient, notably another antidepressant such as a lithium salt, a tricyclic antidepressant, a monoamine oxidase inhibitor or an inhibitor of the reuptake of serotonin, for example.

The invention also concerns a method of treatment of mood disorders, more particularly, a method of treating depression, by administering to the patient an appropriate dose of osanetant or of one of its pharmaceutically acceptable salts.

EXAMPLE 1
Capsule Containing 250 mg of Osanetant

| | |
|---|---:|
| osanetant | 250 mg |
| lactose monohydrate (200 mesh) | 40.80 mg |
| corn (maize) starch | 40.80 mg |
| povidone K-30 | 8.40 mg |
| purified water* | 90.00 mg |
| magnesium stearate | 3.40 mg |
| for an opaque white size-0 capsule, filled to | 343.4 mg |

*evaporated during the drying process after the wet granulation.

EXAMPLE 2
Capsule Containing 100 mg of Osanetant

| | |
|---|---:|
| osanetant | 100 mg |
| lactose monohydrate (200 mesh) | 115.80 mg |
| corn (maize) starch | 115.80 mg |
| povidone K-30 | 8.40 mg |
| purified water* | 90.00 mg |
| magnesium stearate | 3.40 mg |
| for an opaque white size-0 capsule, filled to | 343.4 mg |

*evaporated during the drying process after the wet granulation.

What is claimed is:

1. A method for the treatment of depression or depressive disorders which comprises administering to a patient in need of such treatment an effective amount of osanetant or a pharmaceutically acceptable salt thereof.

2. A method according to claim 1 for the treatment of depression.

3. A method according to claim 1 for the treatment of major depressive disorders.

4. A method according to claim 1 for the treatment of dysthymia.

5. A method according to claim 1 for the treatment of minor depressive disorders.

6. A method according to claim 1 for the treatment of depressive disorders associated with anxiety.

7. A method according to claim 1 for the treatment of depressive disorders associated with bipolar disorders.

* * * * *